US006387614B1

(12) United States Patent
Cheng et al.

(10) Patent No.: US 6,387,614 B1
(45) Date of Patent: May 14, 2002

(54) METHODS FOR USING REDOX LIPOSOME BIOSENSORS

(75) Inventors: Quan Cheng, SF; Raymond C. Stevens, La Jolla, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/608,788

(22) Filed: Jun. 30, 2000

Related U.S. Application Data
(60) Provisional application No. 60/142,861, filed on Jul. 7, 1999.

(51) Int. Cl.[7] .................................................. C12Q 1/00
(52) U.S. Cl. .................... 435/4; 435/5; 435/6; 435/7.1; 435/7.2; 435/7.21; 435/7.31; 435/7.32; 435/7.37; 436/501; 436/518; 436/149; 436/151; 436/801; 436/806; 436/904; 204/403
(58) Field of Search .................. 435/4, 5, 6, 7.1, 435/7.2, 7.21, 7.31, 7.32, 7.37; 436/501, 518, 149, 151, 801, 806, 904; 204/403

(56) References Cited

U.S. PATENT DOCUMENTS 4,849,330 A * 7/1989 Humphries et al. ............ 435/4

OTHER PUBLICATIONS

Scotland et al., "Cytotoxic Enteropathogenic *Escherichia coli*," *Lancet* i:90 [1980].
Farmer and Kelly, "Enterobacteriaceae"in *Manual of Clinical Microbiology*, Balows et al.(eds), American Society for Microbiology, pp. 360–383 [1991].
Pimbly and Patel, "A Review of Analytical Methods for the Detection of Bacterial Toxins," *J. Appl. Microbiol.* (Suppl.), 84:98S–109S [1998].
Mpamugo et al., "Enterotoxigenic *Clostridium perfringens* as a Cause of Sporadic Cases of Diarrhoea," *J. Med. Microbiol.*, 43:442–445 [1995].
Park et al., "Evaluation of a Commercial Enzyme Immunoassay Kit (RIDASCREEN) for Detection of Staphylococcal Enterotoxins A, B, C, D, an E in Foods," *Appl. Environ. Microbiol.*, 60:677–681 [1994].
Charych et al., "Litmus Test" for Molecular Recognition Using Artifical Membranes, *Curr. Biol.*, 3:113–120 [1996].
Dave et al., "Sol–Gel Encapsulation Methods for Biosensors," *Anal. Chem.*, 66:1120A–1127A [1994].
Ohara et al., "Glucose Electrodes Based on Cross–Linked [Os(bpy)$_2$]$^{+/2+}$ Complexed Poly(1–Vinylimidazole) Films," *Anal. Chem.*, 65:3512–3517 [1993].
Gronow, "Biosensors," *Trends Biochem. Sci.*, 9:336–340 [1984].
Finegold and Martin, "General Principles in Staining Procedures," in *Diagnostic Microbiology*, 6th Ed., CV Mosby St. Louis, pp 13–15 [1982].
Spevak, "The Presentation of Biological Ligands on the Surface of Polymerized Monolayers and Liposomes," Ph.D. Thesis, University of California, Berkeley [1993].
Cheng and Stevens, "Coupling of an Induced Fit Enzyme to Polydiacetylene Thin Films: Colorimetric Detection of Glucose." *Adv. Mater.*, 9:481–483 [1997].
Dahms, "Electronic Conduction in Aqueous Solution," *J. Phys. Chem.*, 72:362–365 [1968].
Ruff and Friedrich, "Transfer Diffusion. I. Theoretical," *J. Phys. Chem.*, 75:3297–3302 [1971].

(List continued on next page.)

*Primary Examiner*—Jeffrey Stucker
(74) *Attorney, Agent, or Firm*—Medlen & Carroll, LLP

(57) ABSTRACT

The present invention provides methods and compositions for detecting the presence of biologically-important analytes by using redox liposome biosensors. In particular, the present invention provides liposome/sol-gel electrodes suitable for the detection of a wide variety of organic molecules, including but not limited to bacterial toxins.

19 Claims, 8 Drawing Sheets

OTHER PUBLICATIONS

Cheng and Stevens, "Charge–Induced Chromatic Transition of Amino Acid–Derivatized Polydiacetylene Liposomes," *Langmuir* 14:1974–1976 [1998].

Cheng et al., "Signaling of *Escherichia coli* Enterotoxin on Supramolecular Redox Bilayer Vesicles" *J. Am. Chem. Soc.*, 121:6767–6768 [1999].

Peng et al., "Amperometric Detection of *Escherichia coli* Enterotoxin by Redox Diacetylenic Vesicles on a Sol–Gel Thin Film Electrode," *Anal. Chem.*, 72:1611–1617 [2000].

* cited by examiner

METHODS FOR USING REDOX LIPOSOME BIOSENSORS

This application claims benefit under 35 U.S.C. §120 of provisional patent U.S. Ser. No. 60/142,861, filed on Jul. 7, 1999, which is herein incorporated by reference in its entirety for all purposes.

The present invention was made under work supported by the U.S. Department of Energy under DOE Contract No.: DE-AC03-76SF00098. The government has certain rights in this invention.

FIELD OF THE INVENTION

The present invention provides novel methods and compositions for preparing and using electrochemical sensors to signal the presence of biological molecules.

BACKGROUND OF THE INVENTION

Bacterial toxins are a primary cause of a variety of human diseases. For instance, some strains of *Escherichia coli* residing in the intestines of man and many other animals are capable of secreting various enterotoxigenic toxins. Indeed, these toxigenic strains of *E. coli* are generally considered as a cause of many diarrheal diseases (Scotland et al., Lancet i:90 [1980]). *E. coli* is the organism most commonly isolated in clinical microbiology laboratories, as it is usually present as normal flora in the intestines of humans and other animals. However, it is an important cause of intestinal, as well as extraintestinal infections. For example, in a 1984 survey of nosocomial infections in the United States, *E. coli* was associated with 30.7% of the urinary tract infections, 11.5% of the surgical wound infections, 6.4% of the lower respiratory tract infections, 10.5% of the primary bacteremia cases, 7.0% of the cutaneous infections, and 7.4% of the other infections (Farmer and Kelly, "Enterobacteriaceae," in *Manual of Clinical Microbiology*, Balows et al.(eds), American Society for Microbiology, [1991], p. 365). Surveillance reports from England, Wales and Ireland for 1986 indicated that *E. coli* was responsible for 5,473 cases of bacteremia (including blood, bone marrow, spleen and heart specimens); of these, 568 were fatal. For spinal fluid specimens, there were 58 cases, with 10 fatalities (Farmer and Kelly, supra, at p. 366). There are no similar data for United States, as these are not reportable diseases in this country.

3Studies in various countries have identified certain serotypes (based on both the O and H antigens) that are associated with the four major groups of *E. coli* recognized as enteric pathogens. Table 1 lists common serotypes included within these groups. The first group includes the classical enteropathogenic serotypes ("EPEC"); the next group includes those that produce heat-labile or heat-stable enterotoxins ("ETEC"); the third group includes the enteroinvasive strains ("EIEC") that mimic Shigella strains in their ability to invade and multiply within intestinal epithelial cells; and the fourth group includes strains and serotypes that cause hemorrhagic colitis or produce Shiga-like toxins (or verotoxins) ("VTEC" or "EHEC" [enterohemmorrhagic *E. coli*]).

TABLE 1

Pathogenic *E. coli* Serotypes

| Group | Associated Serotypes |
| --- | --- |
| Enterotoxigenic (ETEC) | O6:H16; O8:NM; O8:H9; O11:H27; O15:H11; O20:NM; O25:NM; O25:H42; O27:H7; O27:H20; O63:H12; O78:H11; O78:H12; O85:H7; O114:H21; O115:H21; O126:H9; O128ac:H7; O128ac:H12; O128ac:H21; O148:H28; O149:H4; O159:H4; O159:H20; O166:H27; and O167:H5 |
| Enteropathogenic (EPEC) | O26:NM; O26:H11; O55:NM; O55:H6; O86:NM; O86:H2; O86:H34; O111ab:NM; O111ab:H2; O111ab:H12; O111ab:H21; O114:H2; O119:H6; O125ac:H21; O127:NM; O127:H6; O127:H9; O127:H21; O128ab:H2; O142:H6; and O158:H23 |
| Enteroinvasive (EIEC) | O28ac:NM; O29:NM; O112ac:NM; O115:NM; O124:NM; O124:H7; O124:H30; O135:NM; O136:NM; O143:NM; O144:NM; O152:NM; O164:NM; and O167:NM |
| Verotoxin-Producing (VTEC)) | O1:NM; O2:H5; O2:H7; O4:NM; O4:H10; O5:NM; O5:H16; O6:H1; O18:NM; O18:H7; O25:NM; O26:NM; O26:H11; O26:H32; O38:H21; O39:H4; O45:H2; O50:H7; O55:H7; O55:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O157:H7; O163:H19; O165:NM; O165:19; and O165:H25 |

Detection of these toxins commonly involves the use of biological (i.e., animal) assays and immunoassays (for review, See, Jay (ed.), *Modern Food Microbiology*, Chapman and Hall, New York [1996]). Bioassays typically involve whole- or part-animal test, which are expensive and require a few days to complete. Imunological assays, on the other hand, couple antibody binding with optical signaling and amplification. The assay time can be reduced to one day or a few hours, depending on the type of method and toxin involved. Currently, various immunoassays are available for bacterial toxins include gel diffusion, reverse passive latex agglutination (RPLA) and enzyme-linked immunosorbent assay (ELISA) (See e.g., Pimbly and Patel, J. Appl. Microbiol. (Suppl.), 84:S98 [1998]). However, these techniques do not give results in a real-time detection fashion. In addition, RPLA can be affected by non-specific interference from materials which physically interfere the formation of a tight button (Mpamugo et al., J. Med. Microbiol., 43:442 [1995]), while ELISA is subject to enzymatic interference from samples containing peroxidase (Park et al., Appl. Environ. Microbiol., 60:677 [1994]). Poor antibody stability limits the use of these methods in field applications. An alternative approach for toxin detection involves the use of the polymerase chain reaction (PCR) to detect the bacterial gene(s) responsible for the production and release of toxins. While highly specific and sensitive, results from PCR may be inconclusive, as the gene may be present, but the toxin may be absent when the organisms are killed. Furthermore, inhibitors of DNA polymerases found in some samples may interfere with the detection of toxin.

Clearly, there is a need for fast, reliable, specific and sensitive methods for the detection of bacterial toxins for use in outbreak investigations, clinical diagnostics and quality monitoring in the food and feed industries. Recent progress in toxin detection methods has primarily focused on supramolecular assemblies (e.g., LB [Langmuir-Blodgett] monolayers and lipid bilayer membranes) coupled with specific cell surface receptors (See e.g., Charych et al., Chem. Biol., 3:113 [1996]). It has been shown that by engineering lipid membranes with desirable optical 'reporting' ability, colorimetric detection of cholera toxin (CT) can be achieved. The colorimetric sensor consists of self-assembly of the amphiphilic diacetylenic lipids and cell surface receptor GM1 in forms of LB monolayers and bilayer vesicles. Nonetheless, in spite of improvements in optical sensors, a still greater degree of sensitivity is needed in the art.

SUMMARY OF THE INVENTION

The present invention provides novel methods and compositions for preparing and using electrochemical sensors to signal the presence of biological molecules. It is not intended that the present invention be limited to any particular biological molecule. For example, it is contemplated that the present invention will find use in the detection and/or identification of microorganisms, prions, microbial toxins, antigens and/or antibodies, antigen and antibody complexes, and other suitable compounds or compositions of interest.

In some embodiments, the present invention is directed to novel biosensors for amperometric detection of E. coli heat-labile enterotoxin, in particular, enterotoxin LT. In preferred embodiments, the novel biosensor couples a redox supramolecular assembly with a sol-gel thin film electrode. In particularly preferred embodiments, the sensor utilizes an open platform to host biosensory elements, thereby allowing fast access of the target molecules to the redox vesicles for detection. Compared to other designs involving sol-gel encapsulation of enzymatic centers for biosensing, the diffusion process is greatly improved and molecular access is less restricted in the present invention. The measured apparent diffusion coefficients for lipid ferrocene are about 2–3 orders of magnitude higher than those for redox-doped polymer/gels. The response time and sensitivity can therefore be improved by the enhancement in mass transport.

The present invention also provides methods for using the amperometric biosensor. As described in the Examples below, the amperometric biosensor was demonstrated to have a detection limit of less that 3 parts per million, which is better than that obtained by colorimetric detection.

It is contemplated that the novel electrochemical sensors of the present invention will find use in the development of sensors for biological molecules such as proteins and toxins whose detection has previously relied upon other signaling mechanisms.

The present invention provides methods for measuring biomolecular recognition of at least one toxin by electrochemistry, comprising: providing liposomes having oxidation/reduction receptors selected from the group consisting of glycine-terminated diacetylene lipid, acetylferrocenic diacetylene lipid, and a glycosphingolipid known to be a receptor for at least one toxin; adding a sample suspected of containing at least one toxin to the liposomes; and measuring the anodic current of ferrocene in order to determine the biomolecular recognition of at least one toxin by the liposomes. In some embodiments, the sample is known to contain at least one toxin or other analyte(s), while in others it is unknown whether the sample contains any toxins or analytes at all. In alternative embodiments, at least one of the toxins comprises an enterotoxin. In other embodiments, only enterotoxin is present in the sample. In some preferred embodiments, the enterotoxin is E. coli enterotoxin, while in some particularly preferred embodiments, the receptor is a receptor for 84-kDa E. coli enterotoxin. In further embodiments, the measuring is conducted by voltammetric determination.

The present invention also provides methods measuring biomolecular recognition of a toxin by electrochemistry, comprising: providing liposomes having oxidation/ reduction receptors selected from the group consisting of glycine-terminated diacetylene lipid, acetylferrocenic diacetylene lipid, and a glycosphingolipid known to be a receptor of 84-kDa E. coli enterotoxin, and a sample suspected of containing E. coli enterotoxin; adding the sample to the liposomes; and measuring the anodic current of ferrocene in order to determine the biomolecular recognition of E. coli enterotoxin by the liposomes. In some preferred embodiments, the mixture ratio of glycine-terminated diacetylene lipid, acetylferrocenic diacetylene lipid, and a glycosphingolipid known to be a receptor of 84-kDa E. coli enterotoxin is approximately 4:1:0.25 respectively. In some embodiments, the sample is known to contain E. coli enterotoxin , while in others it is unknown whether the sample contains E. coli enterotoxin. In still further embodiments, the sample may contain E. coli enterotoxin as well as additional toxins or other analytes. In still other embodiments, the measuring is conducted by voltammetric determination.

The present invention further provides methods for measuring biomolecular recognition of an analyte by electrochemistry, comprising: providing liposomes having oxidation/reduction receptors selected from the group consisting of: glycine-terminated diacetylene lipid, acetylferrocenic diacetylene lipid, and a glycosphingolipid known to be a receptor of an analyte, a sample suspected of containing at least one analyte; adding the sample to said liposomes, and measuring the anodic current of ferrocene to determine the biomolecular recognition of the analyte by said liposomes. In some embodiments, the analyte is selected from the group consisting of microorganisms, drugs, receptor ligands, antigens, allergens, ions, hormones, blood components, disease indicators, cell components, antibodies, lectins, enzymes, organic solvents, volatile organic compounds, pollutants, and genetic material. In some embodiments, the sample is known to contain an analyte, while in others it is unknown whether the sample contains an analyte. In still further embodiments, the sample may more than one analyte (e.g., an analyte of particular interest, as well as other analytes, which may or may not be of interest). In yet other embodiments, the microorganism is selected from the group consisting of viruses, bacteria, parasites, fungi, and prions. In some preferred embodiments, the microorganism is a pathogen. In some alternative embodiments involving viruses, the virus is selected from the group consisting of influenza, rubella, varicella-zoster, hepatitis A, hepatitis B, herpes simplex, polio, small pox, human immunodeficiency virus, vaccinia, rabies, Epstein Barr, reoviruses, and rhinoviruses. However, it is not intended that the present invention be limited to any particular virus or analyte.

DESCRIPTION OF THE INVENTION

The present invention provides novel methods and compositions for preparing and using electrochemical sensors to signal the presence of biological molecules. It is not intended that the present invention be limited to any particular biological molecule. For example, it is contemplated that the present invention will find use in the detection and/or identification of microorganisms, prions, microbial toxins, antigens and/or antibodies, antigen and antibody complexes, and other suitable compounds or compositions of interest.

Figure 1A:
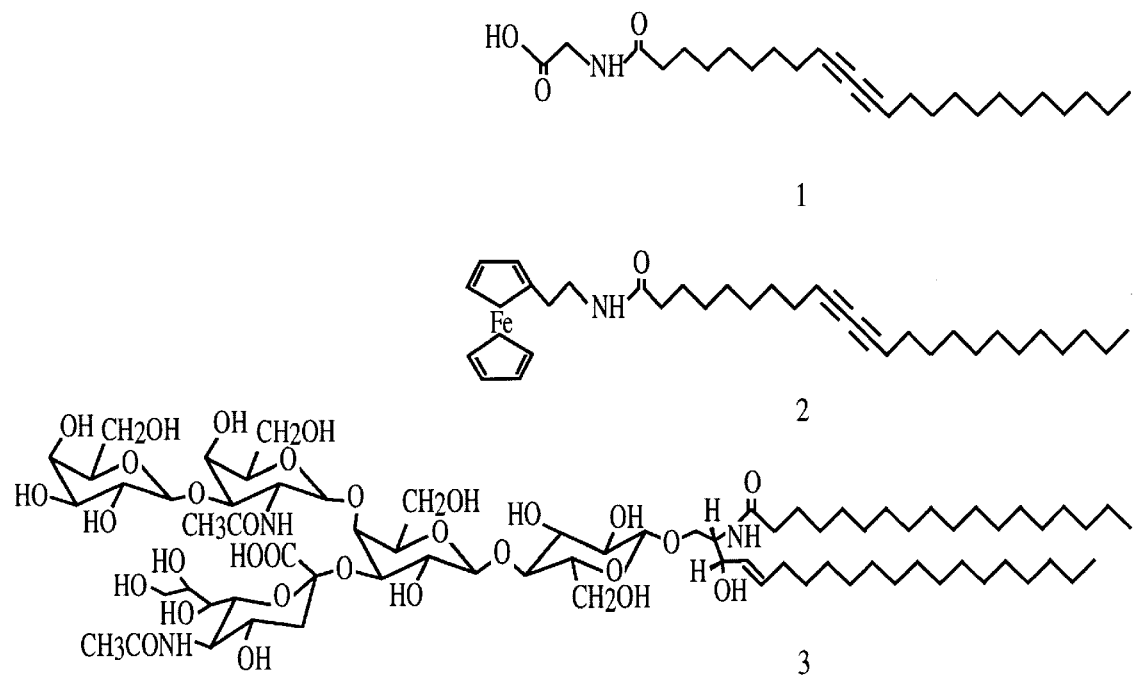
FIG. 1A provides the molecular structure of the lipids and the schematic illustration of the vesicle-based LT biosensor, including
N-(10,12-pentacosadiynoyl)glycine(GLY-PDA) (1);
N-(10,12-pentacosadiynoyl)acetylferrocene(Fc-PDA) (2); and ganglioside GM1 (3).
Figure 1B:
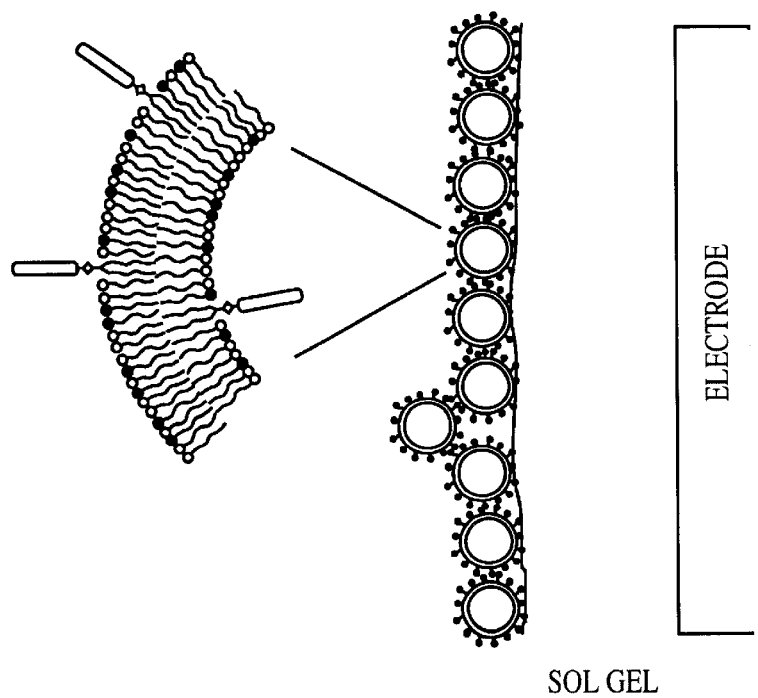
FIG. 1B schematically illustrates the lipid bilayer vesicles attached to a sol gel, and provides a detailed view of the liposome/insulator electrode structure.

The present invention describes for the first time, an amperometric sensor for *Escherichia coli* heat-labile enterotoxin (LT) by redox diacetylenic vesicles on a sol-gel thin film electrode. FIG. 1 provides the molecular structure of the materials and a schematic diagram of the bilayer vesicle sensor for one embodiment of the present invention. The choice of LT as an example target was based on two considerations. First, it demonstrated the feasibility of the design since LT/GM1 is a well-characterized biological system. Thus, it is contemplated that use of the present invention will be extended to other biological toxins and compositions, incuding but not limited to microorganisms, prions, microbial toxins, antigens and/or antibodies, antigen and antibody complexes, and other suitable compounds or compositions of interest using a similar mechanism. Secondly, it is of particular value for use in the clinical and food safety for detecting enterotoxigenic *E. coli* (ETEC), as LT toxin is associated with acute diarrheal disease in humans.

LT toxin is a protein with a molecular weight of 82 kD, consisting of one A subunit (a translocation domain) and five identical B subunits (binding domains). The B subunits bind specifically to cell receptor ganglioside GM1, a glycosphingolipid localized on the cell surface of neurons and intestinal cells. As illustrated in FIG. 1, GM1 contains a carbohydrate recognition group and a hydrophobic ceramide tail, which allows it to be anchored into the cell membrane. Supramolecular assemblies such as monolayers and bilayer vesicles have proven to be an effective method for incorporating GM1 into the desired matrix for characterization and biosensing. During the development of the present invention, diacetylenic lipids derivatized with glycine headgroup (GLY-PDA) for making bilayer vesicles to host GM1 (FIG. 1, compound 1) were used.

One of the problems associated with amperometric detection of proteins is the severe surface fouling of the electrode. Recent research indicates that a layer of sol gel can be effective in preventing protein from denaturing on substrates (Dave et al., Anal. Chem., 66:1120A [1994]). Sol gel, especially organically modified sol gel, has been used extensively on optical sensors detecting biological molecules. Owing to large content of water inside sol gel, it has widely been used to encapsulate biorecognition elements or enzymatic centers. Modification of electrode with sol gel for direct electrochemical communication is rare, mainly because sol gels in general are not conductive. Recently, redox materials have been doped into the gel to acquire electrochemical conductivity through electron hopping (Ohara et al., Anal. Chem., 65:3512 [1993]). During the development of the present invention, it was demonstrated for the first time, that an open platform of gel matrix on an electrode could be used for hosting biosensing elements. Redox lipids were anchored into the bilayer vesicles to provide electrochemical signal, since toxins are electrochemically inactive. The design allowed for direct inspection of the dependency of electron transport on the state and extent of biomolecular recognition that had taken place on the vesicles, and thus provided a method for direct measurement of *E. coli* LT enterotoxin by electrochemistry.

Definitions

To facilitate an understanding of the present invention, a number of terms and phrases are defined below:

As used herein, the term "immobilization" refers to the attachment or entrapment, either chemically or otherwise, of material to another entity (e.g. a solid support) in a manner that restricts the movement of the material.

As used herein, the terms "material" and "materials" refer to, in their broadest sense, any composition of matter.

As used herein, the term "biopolymeric material" refers to materials composed of polymerized biological molecules (e.g., lipids, proteins, carbohydrates, and combinations thereof). Such materials include, but are not limited to, films, vesicles, liposomes, multilayers, aggregates, membranes, and solvated polymers (e.g., polythiophene aggregates such as rods and coils in solvent). Biopolymeric material can contain molecules that are not part of the polymerized matrix (i.e., molecules that are not polymerized).

As used herein the term "protein" is used in its broadest sense to refer to all molecules or molecular assemblies containing two or more amino acids. Such molecules include, but are not limited to, proteins, peptides, enzymes, antibodies, receptors, lipoproteins, glycoproteins, and channels.

As used herein, the term "peptide" refers to any substance composed of two or more amino acids. The term "oligopeptide" refers to a sequence of approximately eight or fewer amino acids.

As used herein, the term "biopolymeric films" refers to polymerized organic films that are used in a thin section or in a layer form. Such films can include, but are not limited to, monolayers and bilayers. Biopolymeric films can mimic biological cell membranes (e.g., in their ability to interact with other molecules such as proteins or analytes).

As used herein, the term "sol-gel" refers to preparations composed of porous metal oxide glass structures. Such structures can have biological or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "direct colorimetric detection" refers to the detection of color changes without the aid of an intervening processing step (e.g., conversion of a color change into an electronic signal that is processed by an interpreting device). It is intended that the term encompass visual observing (e.g., observing with the human eye).

As used herein, the term "analytes" refers to any material that is to be analyzed. Such materials can include, but are not limited to, molecules, bacteria, compounds, viruses, cells, antibodies, and cell parts. In some preferred embodiments, the term refers to microorganisms, drugs, receptor ligands, antigens, ions, hormones, blood components, disease indicators, cell components, antibodies, allergens, lectins, enzymes, organic solvents, volatile organic compounds, pollutants, and genetic material.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s).

As used herein, the term "biosensors" refers to any sensor device that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, Trends Biochem. Sci., 9:336 [1984]).

As used herein, the term "transducer device" refers to a device that is capable of converting a non-electrical phenomenon into electrical information, and transmitting the information to a device that interprets the electrical signal. Such devices can include, but are not limited to, devices that use photometry, fluorimetry, and chemiluminescence; fiber optics and direct optical sensing (e.g. grating couplers); surface plasmon resonance; potentiometric and amperometric electrodes; field effect transistors; piezoelectric sensing; and surface acoustic wave.

As used herein, the term "miniaturization" refers to a reduction in size, such as the size of a sample to increase utility (e.g., portability, ease of handling, and ease of incorporation into arrays).

As used herein, the term "stability" refers to the ability of a material to withstand deterioration or displacement and to provide reliability and dependability.

As used herein, the term "conformational change" refers to the alteration of the molecular structure of a substance. It is intended that the term encompass the alteration of the structure of a single molecule or molecular aggregate (e.g., the change in structure of polydiacetylene upon interaction with an analyte).

As used herein, the term "small molecules" refers to any molecule with low molecular weight (i.e., less than 10,000 atomic mass units and preferably less than 5,000 atomic mass units) that binds to ligands, interacts with ligands, or interacts with biopolymeric material in a manner that creates a conformational change.

As used herein, the term "microorganism" refers to agents including, but not limited to, viruses, bacteria, parasites (including, but not limited to, organisms within the phyla Protozoa, Platyhelminthes, Aschehninithes, Acanthocephala, and Arthropoda), fungi, and prions. The term "pathogen" refers to disease-causing microorganisms or agents.

As used herein, the term "toxin" refers to any compound that has detrimental effects on one or more biological systems. The term encompasses microbial toxins such as endotoxin (e.g., lipopolysaccharide), as well as exotoxins, venoms, and toxins produced by plants and animals. Thus, it is not intended that the present invention be limited to any particular toxin or toxic compound.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, *Diagnostic Microbiology*, 6th Ed. (1982), CV Mosby St. Louis, pp 13–15).

As used herein, the term "membrane" refers to, in its broadest sense, a thin sheet or layer of material. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterols and/or other components. As used herein, the term "membrane fragment" refers to any portion or piece of a membrane. The term "polymerized membrane" refers to membranes that have undergone partial or complete polymerization.

As used herein, the term "polymerization" encompasses any process that results in the conversion of small molecular monomers into larger molecules consisting of repeated units. Typically, polymerization involves chemical crosslinking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "enzyme" refers to molecules or molecule aggregates that are responsible for catalyzing chemical and biological reactions. Such molecules are typically proteins, but can also comprise short peptides, RNAs, or other molecules.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "chromophore" refers to molecules or molecular groups responsible for the color of a compound, material, or sample.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein the term "antibody" refers to a glycoprotein evoked in an aninal by an immunogen (antigen). An antibody demonstrates specificity to the immunogen, or, more specifically, to one or more epitopes contained in the immunogen. The term encompasses antibodies produced in vivo in response to exposure to an immunogen, as well as monoclonal and polyclonal antibodies produced in vitro.

As used herein, the term "chelating compound" refers to any compound composed of or containing coordinate links that complete a closed ring structure.

As used herein, the term "molecular recognition complex" refers to any molecule, molecular group, or molecular complex that is capable of recognizing (i.e., specifically interacting with) a molecule.

As used herein, the term "ambient conditions" refers to the conditions of the surrounding environment (e.g., the temperature of the room or outdoor environment in which an experiment occurs).

As used herein, the term "room temperature" refers, technically, to temperatures approximately between 20 and 25 degrees centigrade. However, as used generally, it refers to the any ambient temperature within a general area in which an experiment is taking place.

As used herein, the terms "home testing" and "point of care testing" refer to testing that occurs outside of a laboratory environment. Such testing can occur indoors or outdoors at, for example, a private residence, a place of business, public or private land, in a vehicle, under water, as well as at the patient's bedside.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the phrase "free floating aggregates" refers to aggregates that are not immobilized.

As used herein, the term "encapsulate" refers to the process of encompassing, encasing, or otherwise associating two or more materials such that the encapsulated material is immobilized within or onto the encapsulating material.

As used herein, the term "optical transparency" refers to the property of matter whereby the matter is capable of transmitting light such that the light can be observed by visual light detectors (e.g., eyes and detection equipment).

As used herein, the term "biologically inert" refers to a property of material whereby the material does not chemically react with biological material.

As used herein, the term "organic solvents" refers to any organic molecules capable of dissolving another substance. Examples include, but are not limited to, chloroform, alcohols, phenols, and ethers.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils.

As used herein, the term "films" refers to any material deposited or used in a thin section or in a layer form.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to artificially produced spherical lipid complexes that can be induced to segregate out of aqueous media.

As used herein, the term "biopolymeric liposomes" refers to liposomes that are composed entirely, or in part, of biopolymeric material.

As used herein, the term "tubules" refers to materials comprising small hollow cylindrical structures.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. "Surfactant molecular assemblies" refers to an assembly of surface active agents that contain chemical groups with opposite polarity, form oriented monolayers at phase interfaces, form micelles (colloidal particles in aggregation colloids), and have detergent, foaming, wetting, emulsifying, and dispersing properties.

As used herein, the term "homopolymers" refers to materials comprised of a single type of polymerized molecular species. The phrase "mixed polymers" refers to materials comprised of two or more types of polymerize molecular species.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors. The term "non-protein ligands" refers to all such ligands with the exception of proteins (defined above).

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the phrase "head group functionality" refers to the molecular groups present an the ends of molecules (e.g., the carboxylic acid group at the end of fatty acids).

As used herein, the term "hydrophilic head-group" refers to ends of molecules that are substantially attracted to water by chemical interactions including, but not limited to, hydrogen-bonding, van der Waals' forces, ionic interactions, or covalent bonds. As used herein, the term "hydrophobic head-group" refers to ends of molecules that self-associate with other hydrophobic entities, resulting in their exclusion from water.

As used herein, the term "carboxylic acid head groups" refers to organic compounds containing one or more carboxyl (—COOH) groups located at, or near, the end of a molecule. The term carboxylic acid includes carboxyl groups that are either free or exist as salts or esters.

As used herein, the term "detecting head group" refers to the molecular group contained at the end of a molecule that is involved in detecting a moiety (e.g., an analyte).

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the phrase "polymeric assembly surface" refers to polymeric material that provides a surface for the assembly of further material (e.g., a biopolymeric surface of a film or liposome that provides a surface for attachment and assembly of ligands).

As used herein, the phrase "chromatic detection element" refers to material that is capable of providing calorimetric analysis (e.g., polymerized diacetylene).

As used herein, the term "formation support" refers to any device or structure that provides a physical support for the production of material. In some embodiments, the formation support provides a structure for layering and/or compressing films.

As used herein, the term "diacetylene monomers" refers to single copies of hydrocarbons containing two alkyne linkages (i.e., carbon/carbon triple bonds).

As used herein, the terms "standard trough" and "standard Langmuir-Blodgett trough" refer to a device, usually made of teflon, that is used to produce Langmuir films. The device contains a reservoir that holds an aqueous solution and moveable barriers to compress film material that are layered onto the aqueous solution (See e.g., Roberts, Langmuir-Blodgett Films, Plenum, New York, [1990]).

As used herein, the term "crystalline morphology" refers to the configuration and structure of crystals that can include, but are not limited to, crystal shape, orientation, texture, and size.

As used herein, the term "domain boundary" refers to the boundaries of an area in which polymerized film molecules are homogeneously oriented. For example, a domain boundary can be the physical structure of periodic, regularly arranged polydiacetylene material (e.g., striations, ridges, and grooves).

As used herein, the term "domain size" refers to the typical length between domain boundaries.

As used the terms "conjugated backbone" and "polymer backbone" refer to the ene-yne polymer backbone of polymerized diacetylenic films that, on a macroscopic scale, appears in the form of physical ridges or striations. The term "polymer backbone axis" refers to an imaginary line that runs parallel to the conjugated backbone. The terms "intrabackbone" and "interbackbone" refer to the regions within a given polymer backbone and between polymer backbones, respectively. The backbones create a series of lines or "linear striations," that extend for distances along the template surface.

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$–$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of light energies arranged in order of wavelength.

As used the term "visible spectrum" refers to light radiation that contains wavelengths from approximately 360 mn to approximately 800 nm.

As used herein, the term "ultraviolet irradiation" refers to exposure to radiation with wavelengths less than that of visible light (i.e., less than approximately 360 nM) but greater than that of X-rays (i.e., greater than approximately 0.1 nM). Ultraviolet radiation possesses greater energy than visible light and is therefore, more effective at inducing photochemical reactions.

As used herein, the term "chromatic transition" refers to the changes of molecules or material that result in an alteration of visible light absorption. In some embodiments, chromatic transition refers to the change in light absorption of a sample, whereby there is a detectable color change associated with the transition. This detection can be accomplished through various means including, but not limited to, visual observation and spectrophotometry.

As used herein, the term "thermochromic transition" refers to a chromatic transition that is initiated by a change in temperature.

As used herein, the term "solid support" refers to a solid object or surface upon which a sample is layered or attached. Solid supports include, but are not limited to, glass, metals, gels, and filter paper, among others. "Hydrophobized solid support" refers to a solid support that has been chemically treated or generated so that it attracts hydrophobic entities and repels water.

As used herein, the phrase "solid sensor platforms" refers to any solid support used for immobilizing sensor material.

As used herein, the term "film-ambient interface" refers to a film surface exposed to the ambient environment or atmosphere (i.e., not the surface that is in contact with a solid support).

As used herein, the term "formation solvent" refers to any medium, although typically a volatile organic solvent, used to solubilize and distribute material to a desired location (e.g., to a surface for producing a film or to a drying receptacle to deposit liposome material for drying).

As used herein, the term "micelle" refers to a particle of colloidal size that has a hydrophilic exterior and hydrophobic interior.

As used herein, the term "topochemical reaction" refers to reactions that occur within a specific place (e.g., within a specific portion of a molecule or a reaction that only occurs when a certain molecular configuration is present).

As used herein, the term "molding structure" refers to a solid support used as a template to design material into desired shapes and sizes.

As used herein, the terms "array" and "patterned array" refer to an arrangement of elements (i.e., entities) into a material or device. For example, combining several types of biopolymeric material with different analyte recognition groups into an analyte-detecting device, would constitute an array.

As used herein the term "interferants" refers to entities present in an analyte sample that are not the analyte to be detected and that, preferably, a detection device will not identify, or would differentiate from the analyte(s) of interest.

As used herein, the term "device" refers to any apparatus (e.g., multi-well plates and badges) that contain biopolymeric material. The biopolymeric material may be immobilized or entrapped in the device. More than one type of biopolymeric material can be incorporated into a single device.

As used herein, the term "halogenation" refers to the process of incorporating or the degree of incorporation of halogens (i.e., the elements fluorine, chlorine, bromine, iodine and astatine) into a molecule.

As used herein, the term "aromaticity" refers to the presence of aromatic groups (i.e., six carbon rings and derivatives thereof) in a molecule.

As used herein, the phrase "water-immiscible solvents" refers to solvents that do not dissolve in water in all proportions. The phrase "water-miscible solvents" refers to solvents that dissolve in water in all proportions.

As used herein, the terms "positive," "negative," and "zwitterionic charge" refer to molecules or molecular groups that contain a net positive, negative, or neutral charge, respectively. Zwitterionic entities contain both positively and negatively charged atoms or groups whose charges cancel (i.e., whose net charge is 0).

As used herein, the term "biological organisms" refers to any carbon-based life forms.

As used herein, the term "in situ" refers to processes, events, objects, or information that are present or take place within the context of their natural environment.

As used the term "aqueous" refers to a liquid mixture containing water, among other components.

As used herein, the term "solid-state" refers to reactions involving one or more rigid or solid-like compounds.

As used herein, the term "regularly packed" refers to the periodic arrangement of molecules within a compressed film.

As used herein, the term "filtration" refers to the process of separating various constituents within a test sample from one another. In one embodiment, filtration refers to the separation of solids from liquids or gasses by the use of a membrane or medium. In alternative embodiments, the term encompasses the separation of materials based on their relative size.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals, food, feed, and industrial samples. These examples are not to be construed as limiting the sample types applicable to the present invention.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); $\mu$Ci (microcurie); mN (millinewton); Å (angstrom); kDa (kilodalton); ppm (parts per million); min. (minute or minutes); hr. (hour or hours); N (newton); ° C. (degrees Centigrade); wt % (percent by weight); aq. (aqueous); J (Joule); UV (ultraviolet); XPS (x-ray photoelectron spectroscopy); Fc (ferrocene); PDA (diacetylene monomer); GLY-PDA (N-(10,12-pentacosadiynoyl) glycine); Fc-PDA (N-(10,12-pentacosadiynoly)acetylferrocene); GM1 (ganglioside GM1); PCA (pentacosadiynoic acid monomer); DCDA (docosadynoic acid); SA-PDA (sialic acid-derived PDA); OTS (octadecyltrichlorosilane); CR (calorimetric response); pH (hydrogen ion concentration); EDC (ethylcarboiimide hydrochloride); PBS (phosphate buffered saline); AFM (atomic force microscope); ESEM (environmental scanning electron microscope or microscopy); TEM (transmission electron microscopy or microscope); BSA (bovine serum albumin); Hz (Hertz); LB (Langmuir-Blodgett); NHS (N-hydroxy succinimide); $CO_2$ (carbon dioxide); $MgSO_4$ (magnesium sulfate); $CdCl_2$ (cadmium chloride); MeOH (methanol); Be (beryllium ions); Mg (magnesium ions); Ca (calcium ions); Ba (barium ions); $N_2$ (nitrogen gas); Sigma (Sigma Chemical Co., St. Louis, Mo.); Perkin-Elmer (Perkin-Ehner Co., Norwalk, Conn.); Fisher (Fisher Scientific, Pittsburgh, Pa.); and Farchan Laboratories (Farchan Laboratories, Inc., Gainesville, Fla.); Park Scientific Instrument (Park Scientific Instruments, Sunnyvale, Calif.); Biorad (Bio-Rad Laboratories, Hercules, Calif.); Gelman (Gelman Sciences, Ann Arbor, Mich.); Pierce (Pierce, Rockford, Ill.); and Bellco Glass (Bellco Glass Inc., Vineland, N.J.).

Cyclic voltammetric and chronocoulometric measurements were carried out with a Bioanalytical Systems (BAS) CV-50 W voltammetric analyzer. An EG&G model 362 scanning potentiostat in connection with an EG&G model RE0089 X-Y recorder was used for some voltammetric determinations. A glassy carbon electrode (BAS, 3 mm in diameter) was used as the basic working electrode, with Ag/AgCl (BAS, in 3 M NaCl) as reference and a platinum wire (BAS) as the count electrode. The solution was stirred by a magnetic stirrer during the binding time.

Monosialoganglioside (GM1) was purchased from Matreya (Pleasant Gap, Pa.) and its purity was more than 98% according to the manufacturer. *E. coli* heat-labile enterotoxin (LT) and bovine serum albumin (BSA) were purchased from Sigma. Both were used as received. Ferrocylacetonitrile (Aldrich), lithium aluminum hydride (Aldrich) and 10,12-pentacosadiynoic acid (Farchan, Gainesville, Fla.) were used to synthesize ferrocylpentacosadiynoic acid (Fc-PDA). Tetraethoxysilane (TEOS) used for the preparation of sol-gel was from Fluka. All solutions were prepared in double distilled deionized water purified with a Nanopure Water System, and most other chemicals were of reagent grade (unless stated otherwise).

Example 1

Synthesis of Fc-PDA and Liposomes

In this Example, methods for the synthesis of Fc-PDA and liposomes is described. Fc-PDA lipid was synthesized through amidization of ferrocenoethylamine with N-hydroxysucinimidyl (NHS)-PDA by modification of a previous procedure (Spevak, Ph.D. Thesis, University of California, Berkeley [1993]). Briefly, ferrocenoethylamine was prepared by reduction of ferroceneacetonitrile in the presence of lithium aluminum hydride. Ferroceneacetonitrile in ether was added dropwise to excess lithium aluminum hydride in ether. The mixture was stirred at room temperature overnight. The excess LiAlH$_4$ was destroyed by addition of moist ether. After addition of water, the mixture was separated, and the organic layer was dried and evaporated to give the brown oily product. NHS-PDA was prepared by a previously reported method (Cheng et al., Adv. Mater., 9:481 [1997]).

In short, 0.345 g of N-hydroxysuccinimide was added to 1 g of PDA in 10 ml of dichloromethane, followed by 0.596 g of 1-[3-(dimethylamino)propyl]-3-ethylcarbodiimide hydrochloride (DEC). The solution was allowed to stir at ambient temperature for 2 hours folliwnged by rotary evaporation of the dichloromethane. The product was extracted with ethyl acetate and water. The organic layer was dried with MgSO$_4$, filtered, and the solvent was removed by rotary evaporation to give a white solid. Mass spectrometry confirmed the structure.

Approximately equal moles of ferrocenoethylamine and NHS-PDA were then carefully mixed in chloroform and mildly stirred using a magnetic bar at room temperature for 2 hours. The mixture was then concentrated, applied to a silica gel column (Merck grade 9385, 230–400 mesh), and eluted by a mixed solvent of 4:1 CHCl$_3$/MeOH (v:v). The product collection was evaporated and confirmed by mass spectrometry (FAB$^+$, 585.5).

The bilayer vesicles (i.e., liposomes) used for constructing LT biosensors were prepared by probe sonication of related lipids in a buffer solution. Three lipids (GLY-PDA, Fc-PDA and GM1, provided in a 4:1:0.25 molar ratio) in chloroform were mixed in a small amber vial. The organic solvent was then removed by flowing a N$_2$ stream over the mixture, to form a thin lipid layer on the bottom. Appropriate amount of a buffer of 20 mM HEPES containing 0.15 M NaCl at pH 7.5, was added so that the final lipid concentration was approximately 0.5 mg/ml. The solution was sonicated using low amplitude at room temperature for 20 min. The conditions had to be carefully optimized so that the temperature would not exceed 70° C. during the process, as this would damage the binding activity of GM1. Sonication produced a clear solution, which was allowed to cool to room temperature before being put into a refrigerator (4° C.) for liposome formation and storage. Transmission electron microscopy (TEM) was used to characterize the solution and confirmed the formation of liposomes that came with typical dimensions from 100 to 200 nm in diameter.

Example 2

Liposome/Sol-Gel Thin Film Fabrication

In this Example, the fabrication of liposome/sol-gel thin films is described. A sol-gel stock solution was prepared by mixing 2.25 ml TEOS, 0.8 ml ethanol, 1.4 ml 0.1 M KCl, and 50 $\mu$l 0.05 M HCl. The mixed solution was stirred for 3 hours and a clear solution resulted. About 10 $\mu$l of this solution was pipetted and spread carefully on the surface of glassy carbon electrode (3 mm in diameter, from Bioanalytical System) using a pin. The solution residue on the plastic sealing of the electrode was carefully removed using cloth. After gelation of the stock solution in a couple of minutes, a colorful film was observed due to optical diffraction. The liposome solution (~10 $\mu$l) was pipetted onto the sol-gel thin film surface and allowed to adsorb for 10 min. After rinsing, liposome/sol-gel electrodes were kept in a PBS solution until used.

Example 3

Electrochemical Procedures

In this Example, electrochemical procedures used during the development of the present invention are provided. Voltammetric measurements were performed in a 0.1 M PBS solution (pH 7.4). The sensor electrode was scanned with a linear potential sweep from 0.0 V to 0.7 V with a scan rate of 200 mV/s and the peak current was measured as $S_{100}$. The electrode was then transferred into the sample solution to bind with the toxin for a given time. The toxin-bound biosensor was returned to the original PBS solution for voltammetric determination, and the current response was measured as $S_x$. The normalized signal response was calculated as $(S_x/S_{100}) \times 100\%$.

Chronocoulometric measurements were performed on a sensor electrode coated with liposome/sol gel film with a potential step from 0.4 V to 0.7 V. The pulse width of 5 s. Anson plots (i–t$^{1/2}$) were converted from plots of current versus, time by CV-50 W voltammetric analyzer.

Example 4

Electrochemical Characterization of Bilayer Vesicles Containing Fc-PDA

Figure 2:
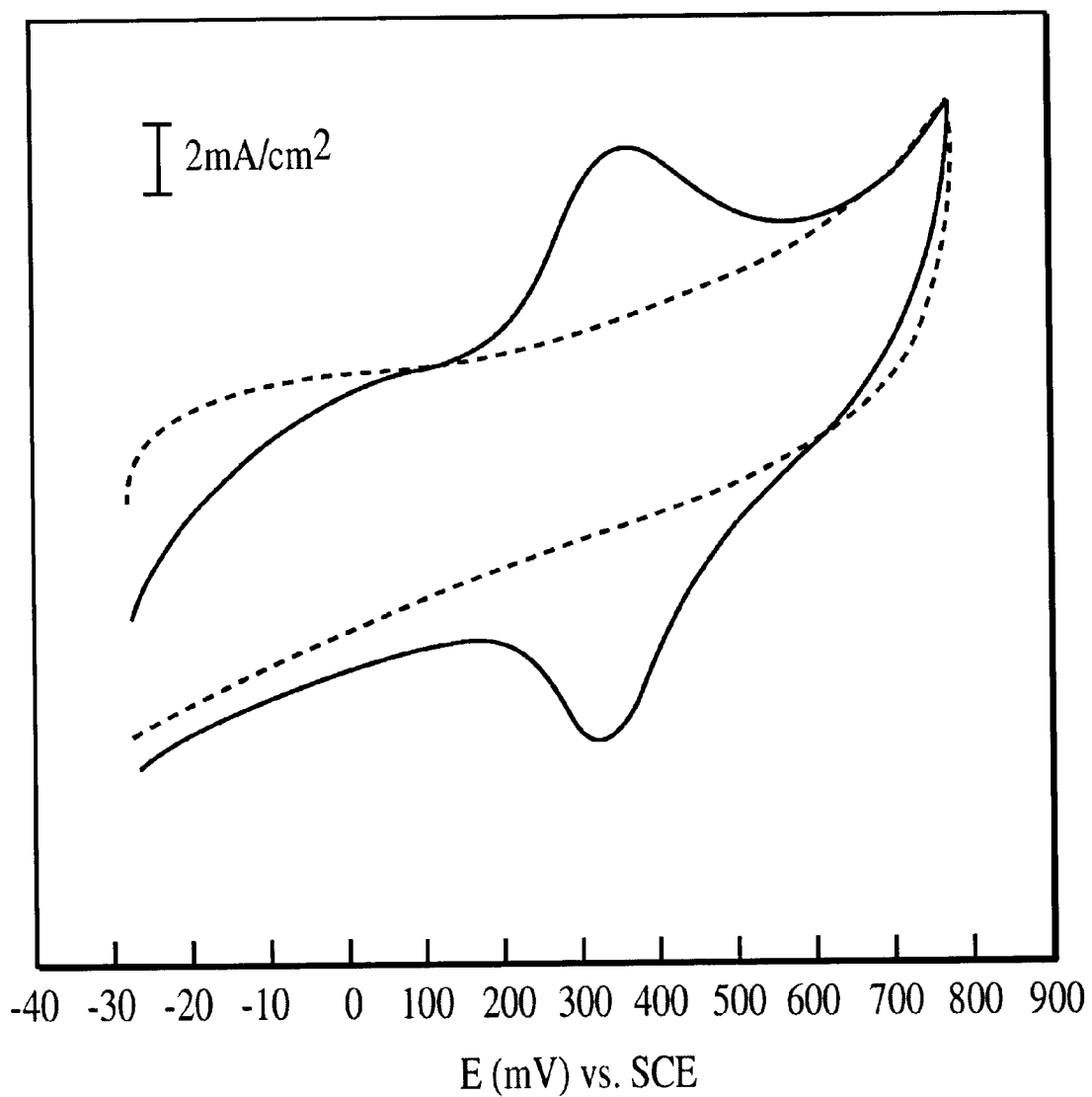
FIG. 2 shows cyclic voltammograms of the vesicle/sol-gel electrodes without Fc-PDA (indicated by dashed lines) and with Fc-PDA (indicated by solid lines) in 0.1 M, pH 7.4 PBS solution. The potential scans ran from −0.3 V to 0.8 V and the scan rate was 200 mV/s.
Figure 3:
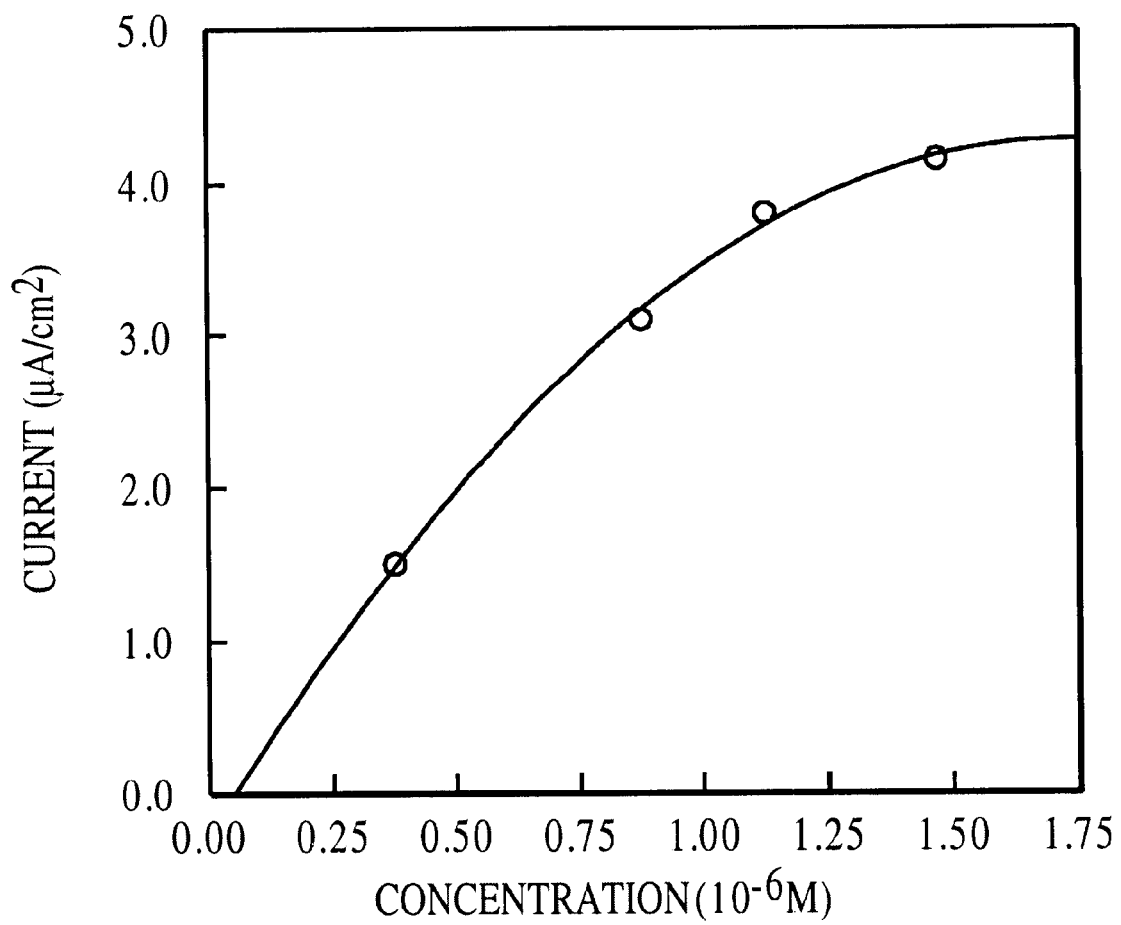
FIG. 3 illustrates the effect of the concentration of Fc-PDA in liposomes on peak current in a PBS solution. The potential scans range from −0.3 V to 0.8 V and the scan rate was 200 mV/s.
Figure 4:
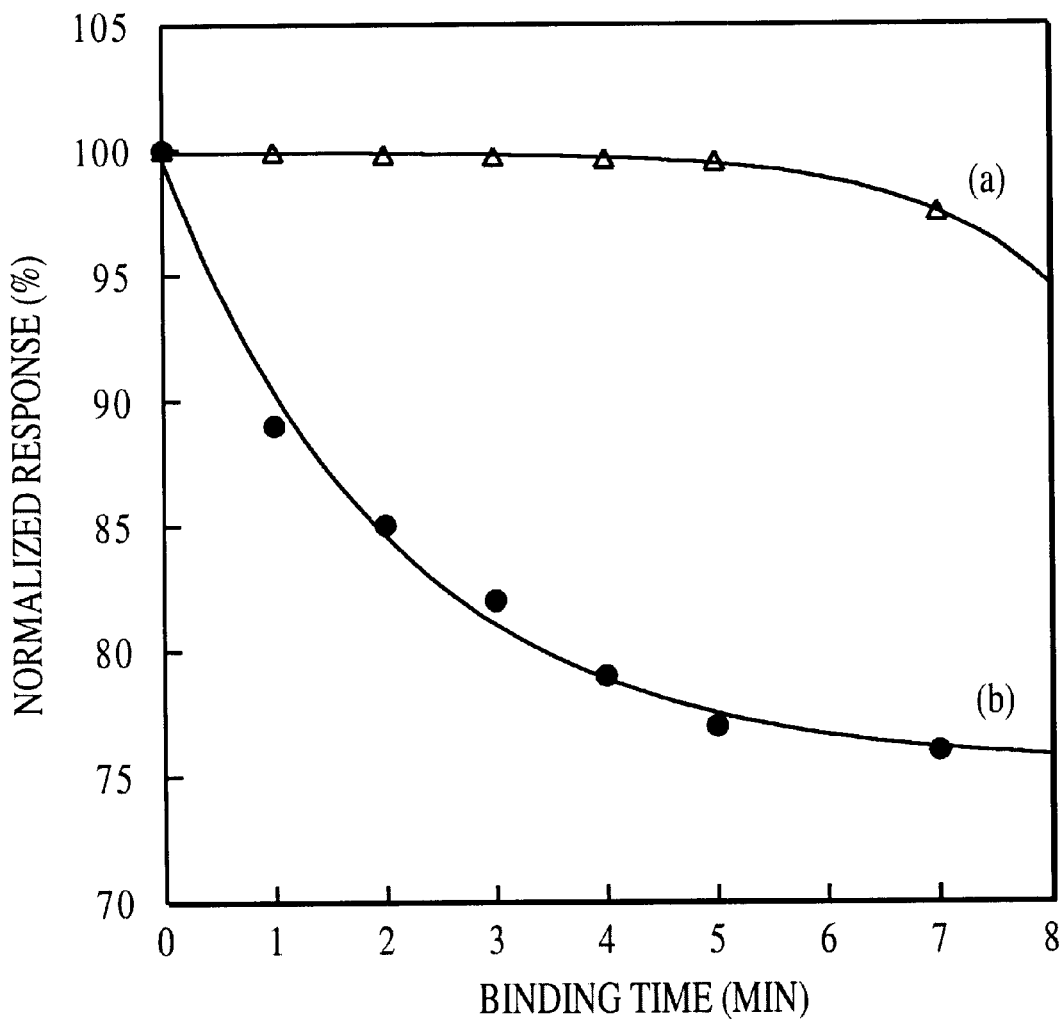
FIG. 4 illustrates the effect of the binding time on voltammetric response of the vesicle/sol-gel electrodes in PBS solutions. In this graph, (a) represents $1 \times 10^{-3}$ g/ml of BSA (triangles), and (b) represents $8 \times 10^{-5}$ g/ml of E. coli LT toxin (circles). The concentration of Fc-PDA in vesicles was $1.5 \times 10^{-6}$ M.
Figure 5:
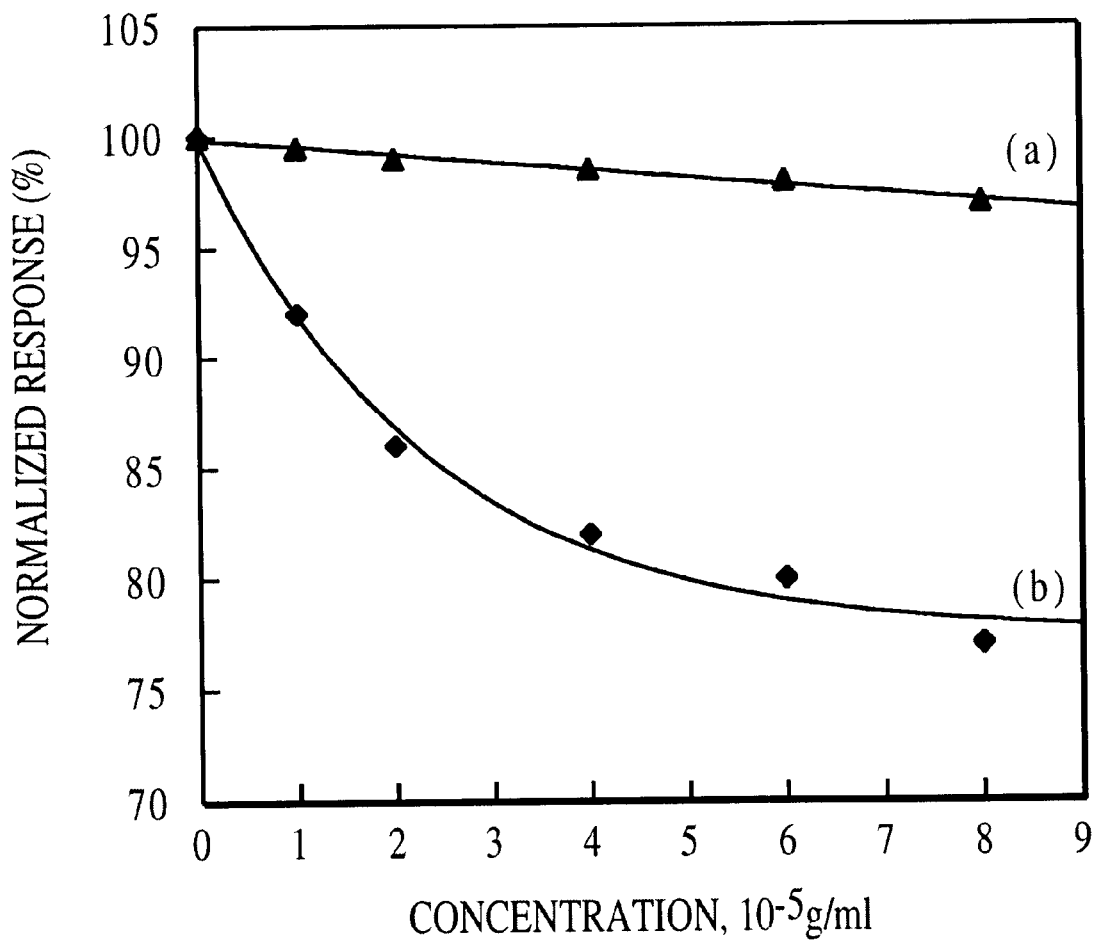
FIG. 5 illustrates the effect of E. coli LT toxin concentration on voltammetric response of the sensor without the receptor (a) and with the receptor (b). The binding time was 5 min for both cases. The concentration of Fc-PDA in vesicles was $1.5 \times 10^{-6}$ M. In this Figure, the triangles correspond to the response of the sensor without the receptor incorporated, while the diamonds correspond to the response of the sensor with the receptor incorporated.

In this Example, results from experiments to determine the electrochemical characterization of bilayer vesicles containing Fc-PDA are described. As the liposome/sol gel sensor used in this work was based on supramolecular assemblies containing a redox probe and receptor that binds with LT toxin, a facile redox reaction of Fc-PDA on bilayer vesicles is important for successful operation of the preferred embodiments of the invention. FIG. 2 shows cyclic voltammograms of vesicles adsorbed on the sol-gel thin film electrode in a 0.1 M, pH 7.4 PBS solution. Well-defined current response was obtained for Fc-PDA containing vesicles on the electrode. In the absence of the redox-active Fc-PDA, however, no voltammetric response was observed for the adsorbed vesicles (not shown). The current peaks show diffusion characteristics. The peak separation between the anodic and cathodic current is about 60 mV, which is considerably lower than what one would expect on a sol gel film electrode, indicating that the redox reactions for the vesicles are chemically reversible. For one particular concentration ($1.5\times10^{-6}$ M) of FC-PDA, the current density was found to be capable of reaching 4.29 $\mu A/cm^2$, demonstrating a high level of sensitivity for this electrochemical operation.

The concentration of Fc-PDA in the vesicles adsorbed on the sol gel film were found to be capable of influencing the electrochemical sensitivity of the sensor. This was shown by experiments in which the amount of Fc-PDA incorporated into vesicles was varied, and the effect of Fc-PDA concentration on voltammetric response was tested. FIG. 3 shows the current magnitude as a function of Fc-PDA concentration in vesicles. The current signal increases upon raising the Fc-PDA concentration in vesicles and eventually levels off at high concentration, indicating saturation of the electrochemical response for the adsorbed redox vesicles. It appeared to that the high peak current of the sensor in the saturation region provided no benefit in terms of lowering the detection limit in measurements. A concentration of $1.5\times10^{-6}$ M Fc-PDA was therefore used to fabricate the sensors for most of the experiments reported here. The saturation may come from the structure change associated with the high content of Fc-PDA in the vesicles. It was observed that vesicle making was made progressively difficult when the ratio of GLY-PDA:Fc-PDA went below 2:1. It is believed that such an observation is closely related to the headgroup structure of Fc-PDA since Fc unit is strongly hydrophobic.

Example 5

Voltammetric Detection of LT Binding on Vesicles

In this Example, experiments involving LT binding on vesicles and the voltammetric detection of bound LT are described. The *E. coli* LT toxin sensor was first tested to determine the optimal binding time required for the detection of LT toxin. FIG. 4 shows the effect of binding time on the amperometric response of the sensors in LT toxin solutions and the BSA solution that served as a control. There was no change of current in 5 minutes when a biosensor was inserted in a $1\times10^{-3}$ g/ml BSA solution (as shown in FIG. 4A). However, the amperometric response of the sensor decreased noticeably when the electrode was placed in a PBS solution containing $8\times10^{-5}$ g/ml of the toxin (as shown in FIG. 4B). The amperometric signal decreased exponentially with the binding time within the first 5 minutes and then gradually slowed down. The longer the binding time, the more the current decreased. The response leveled off after about 7 minutes. An almost 24% decrease in the current was found for the sensor after 7 min. These results clearly demonstrate that the toxin molecules in the solution diffuse onto the electrode surface and interact with the receptor on vesicles. It is believed that the formed complex between the receptor and toxin blocked the charge transfer route on the electrode surface, and gradually diminished the current response. Thus, it is contemplated that the sensitivity of the biosensor could be enhanced when longer binding time is used in the measurements. As the response was minimal for other proteins (such as BSA), the sensor was specific to *E. coli* heat-labile enterotoxin.

In order examine the detecting properties of the sensor, two kinds of the sol-gel thin film electrodes (with and without receptor in the vesicles) were prepared and inserted into the different concentrations of the LT toxin solutions. FIG. 5 shows the results. No current change was found on the electrode without the receptor GM1 (as shown in FIG. 5A), demonstrating the important role of GM1 in defining the specificity of the sensor. From an analytical perspective, the background current for the sensor is stable for detection. As for receptor-modified electrodes, the amperometric signal decreased quickly with increasing toxin concentrations. The calibration curve for *E. coli* LT toxin is shown in FIG. 5B. The dynamic range for the assay was found to extend between $0.5\times10^{-5}$ and $8\times10^{-5}$ g/ml. The detection limit of the biosensor has been measured in a $1\times10^{-5}$ g/ml solution. The amperometric signal decreased by 20% after 20 min binding time. A detection limit of $3\times10^{-6}$ g/ml ($3.6\times10^{-8}$ M) (3 PPM) was therefore determined using the 3× standard deviation principle.

The fabrication protocol for combination of receptor and electroactive probe in the vesicles was found to result in good stability and reproducibility. A series of five measurements at different sensors using a $2\times10^{-5}$ g/ml toxin solution resulted in a standard deviation of 8.5%. A negligible loss in the amperometric response was observed over multiscan of potential at the same sensor. The results indicated that retention of the specific binding capability was effective, and the changes in vesicles' microstructure at the biosensor surface were minimal during measurements.

The effect of sol-gel coating on electrodes has also been examined by cyclic voltammetry in the solution with a high concentration of proteins. When the bare glassy carbon electrode was tested in a $5\times10^{-3}$ g,/ml $K_4[Fe(CN)_6]$ solution containing 50 mg/ml of BSA, there was 31% of decrease in voltammetric response and over 80 mV of potential separation between anodic and cathodic peaks, indicating that the electrode surface had been seriously poisoned by protein adsorption. When sol-gel was coated on the electrode surface, the current response was much lower than on the bare electrode. However, there was only 4% of decrease in peak current, and no change in potential separation was observed after addition of BSA. Compared to the bare electrode, this demonstrates that the sol-gel film effectively protects the electrode surface from severe fouling by non-specific adsorption of proteins. The excellent sensor stability suggests that it can be used to analyze complicated sample conditions.

Example 6

Electrode Surface Characterization

In this Example, electrode surface characterization results are described. The sol-gel thin film LT sensor was further characterized by optical, electrochemical and other instrumental methods. When viewed using an optical microscope, the gel layer looks smooth and integral, exhibiting colorful reflective spectrum, possibly as a result of interference of the light reflected from the gel and electrode surface, respectively. Sol gel is known for its superb optical transmission properties. Interestingly, the gel layer on glassy carbon electrode seemed to be more stable than that on the plastic material surrounding the glassy carbon core. The latter forms large cracks and defects that are quite visible when viewed with a optical microscope, indicative of different adhesive property of sol gel on different substrates. The thickness of the gel thin film was determined using SEM by measuring at the edge of the gel layer. The thickness was found to vary slightly from batch to batch, but the average thickness was determined to be around 500 nm. It is interesting to note that the 500 nm-thick sol gel thin film is virtually an insulating layer. An attempt to increase the gel conductivity by replacing water with various aqueous electrolytes to hydrolyze TEOS was also made. However, no noticeable improvements were observed.

Figure 6A:
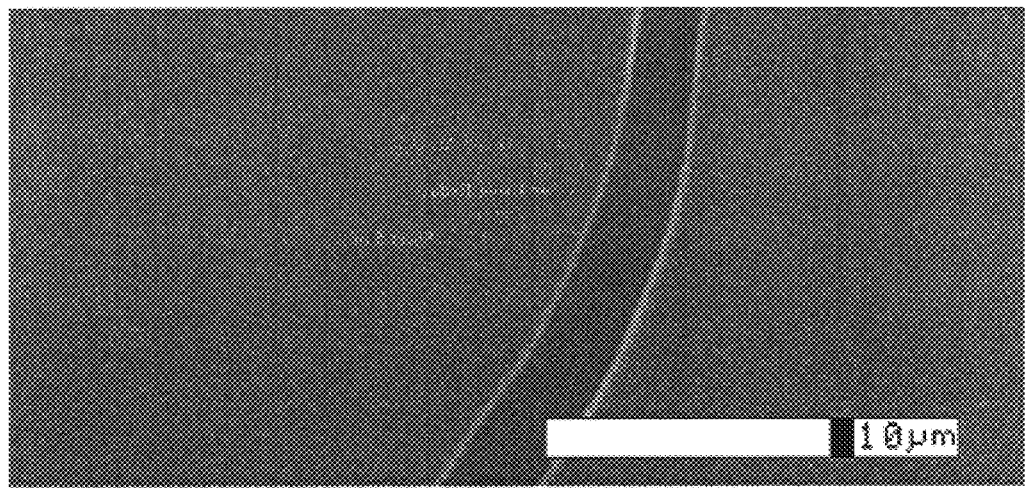
FIG. 6A provides an ESEM image of a sol gel thin film electrode.
Figure 6B:
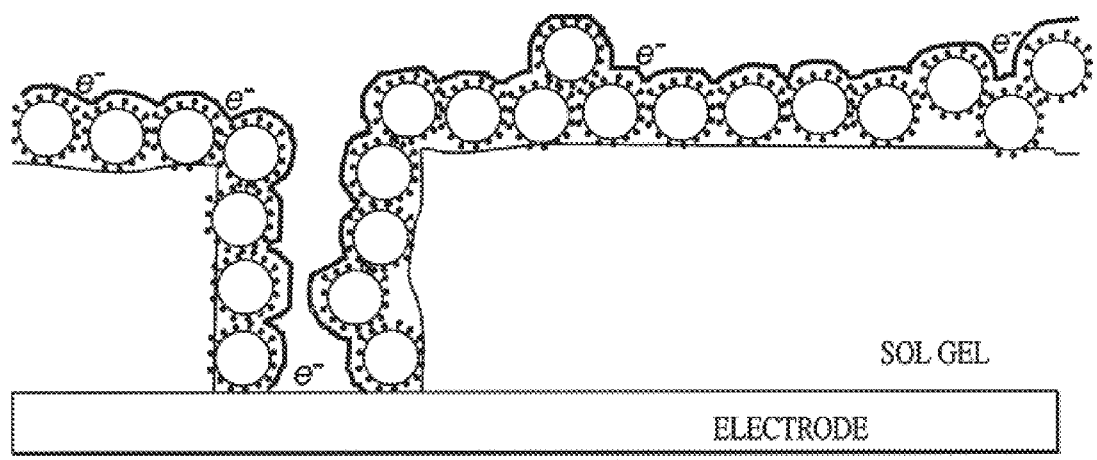
FIG. 6B is a schematic diagram illustrating lateral electron transport on vesicles adsorbed on the sol gel thin film electrodes.
Figure 6C:
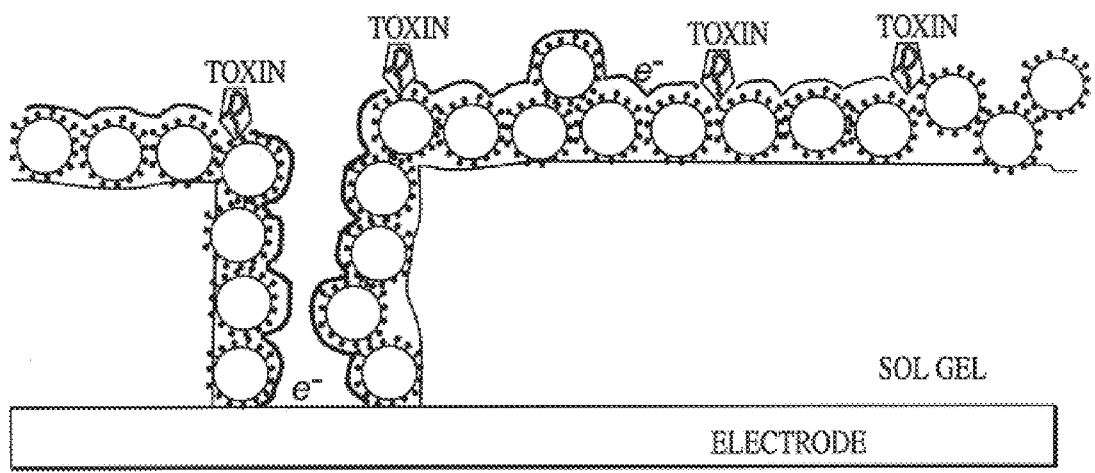
FIG. 6C is a schematic diagram showing current decline as a result of toxin binding that blocks the electron transport path.
Figure 7A:
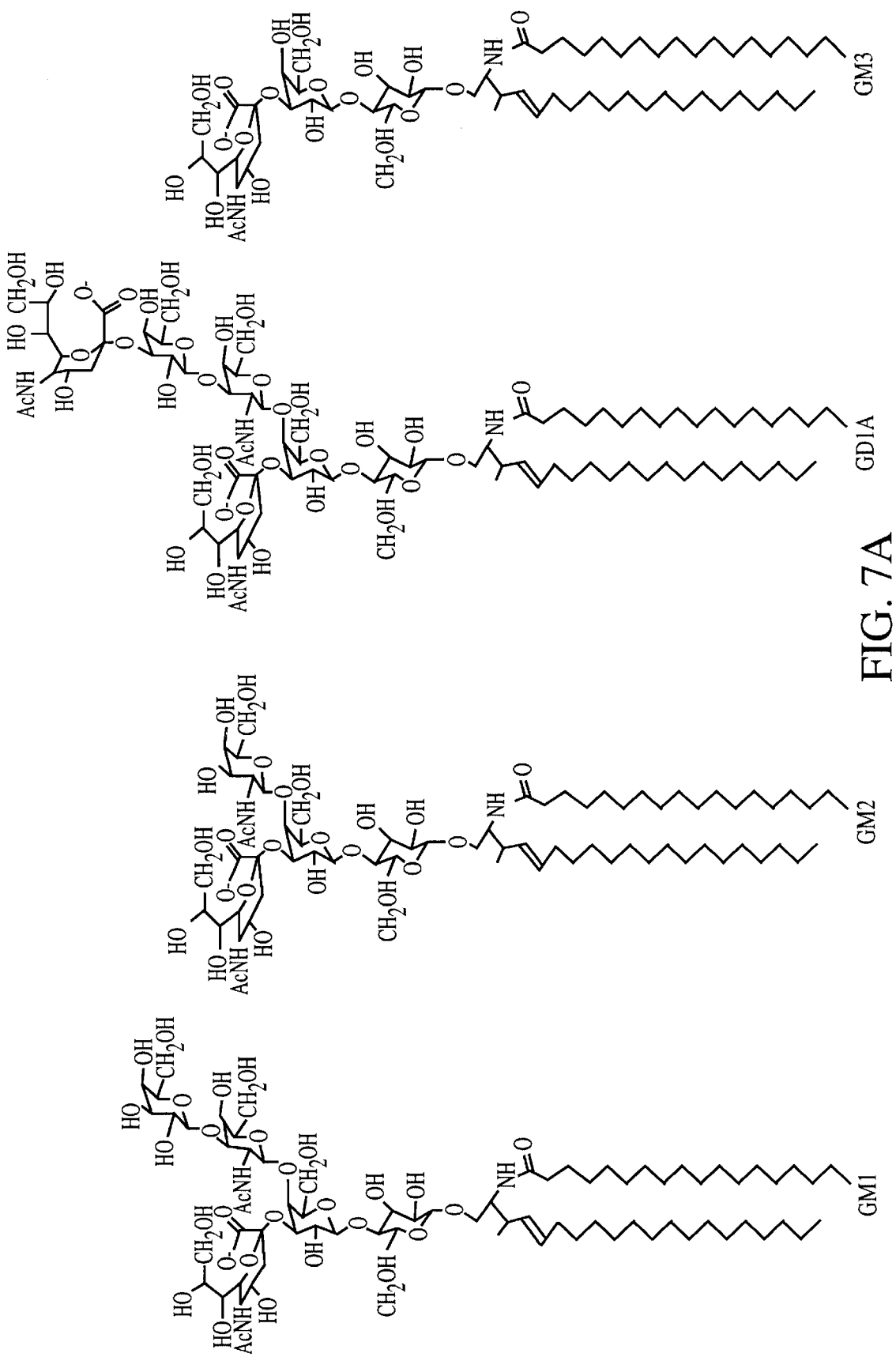
FIG. 7A provides the structures of four gangliosides (GM1, GM2, GD1A, and GM3).
Figure 7B:
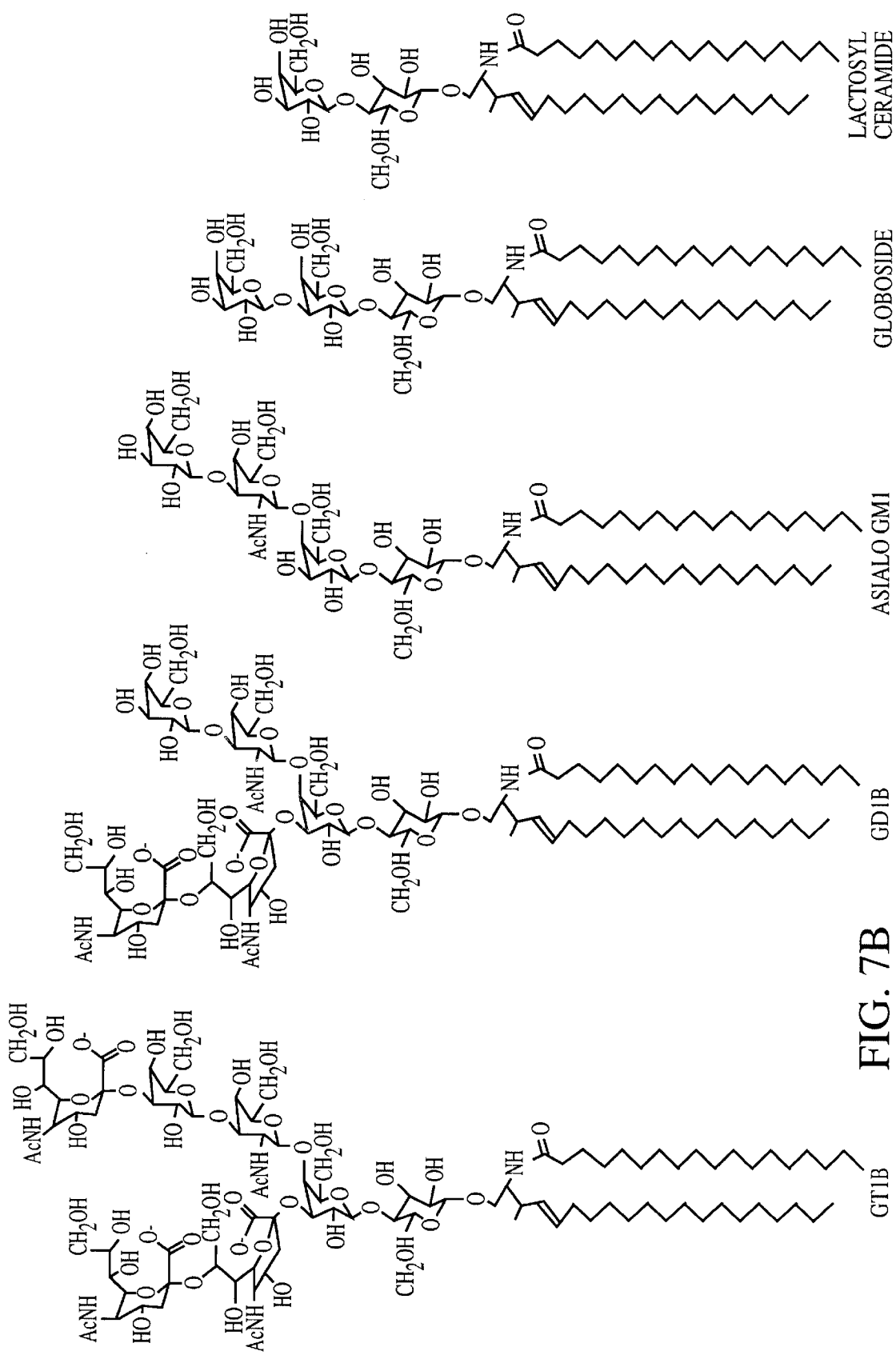
FIG. 7B provides the structures of additional gangliosides (GT1B, GD1B, asialo GM1, globoside, and lactosyl ceramide).

Electrochemical characterization of the gel film was carried out by cyclic voltammetry using $Fe(CN)_6^{4-}$. The results showed that a great portion of current was suppressed, as compared to that on the bare electrode. However, a small portion of redox current for $Fe(CN)_6^{4-}$ was readily obtained. As the peak separation in CV curves was found to be comparable with that on a bare electrode, this suggests the presence of free electrode surface available for redox reaction, presumably from gel cracks. Thus, an Environmental SEM (ESEM) was utilized in order to further characterize the gel thin film on the electrode. ESEM was considered to be advantageous over conventional SEM for this study, since it allows for surface study under much milder conditions. FIG. 6A shows the ESEM image of a sol gel thin film on glassy carbon. The result revealed the presence of microscale cracks on the gel film, occupying less than 1% of the total area. Given the fact that the current for redox liposomes observed on gel surface decreases only slightly as compared to that on the bare electrode, it is obvious that the large current of redox vesicles on the gel-coated electrode is not totally originating from the gel cracks.

In view of these results, a gel crack-assisted electron transport mechanism to explain the large ferrocene current and its response to enterotoxin binding was explored. However, it is noted that an understanding of the mechanism is not necessary in order to use the present invention. The oxidation of ferrocene first occurs on the glassy carbon electrode to the vesicles trapped in the gel cracks, as shown schematically in FIG. 6B. As the concentration of ferrocene becomes depleted at the interface, the process requires, for charge neutrality, ionic migration from the bulk into the area. Since the redox sites are covalently attached to the bulky vesicles, free diffusion of individual ferrocene to electrode is unlikely. However, if only the ferrocene lipids in the vicinity of electrode transfer electrons, the voltammogram would have the feature of surface-confined reaction. Nevertheless, in these experiments, the response is a typical diffusion-control process (See, FIG. 2), indicating that ferrocene species on the gel surface and far from crack sites participate in the electron transfer. When the enterotoxin is added, its binding to the receptor sites on the vesicles blocks the electron transport path, resulting decrease in current magnitude.

The charge transport on a supramolecular assembly is influenced by many factors, including the intrinsic electron transfer between adjacent redox sites, the physical diffusion of electroactive species, the charge compensating counterion motion coupled to electron transfer, the motion of solvent and the segmental motion of surrounding structure. To characterize this complex process, the apparent diffusion coefficient $D_{app}$, which is given by Dahms-Ruff equation (Dahms, J. Phys. Chem., 72:362 [1968]; and Ruff et al., J. Phys. Chem., 75:3297 [1971]) was studied:

$$D_{app}=D_{phys}+k_{ex}C_E\delta^2/6$$

where $D_{phys}$ denotes the diffusion coefficient for physical displacement of the redox species, $k_{ex}$ is the electron self-exchange rate constant, $C_E$ is the concentration of the redox species, and δ is the distance between redox centers at the time of electron transfer. When electron self-exchange makes a significant contribution to the transfer process, $D_{app}$ exhibits a linear dependence on the concentration of electroactive sites frozen inside the films. A zero intercept would point to negligible contribution from $D_{phy}$ as observed for fixed-site redox polymers. Thus, the $D_{app}$ was measured at different redox concentrations by use of potential-step chronocoulometry. The chronocoulometric charge-time transient is described by the following equation:

$$Q=2nFCD_{app}^{1/2}t^{1/2}/\pi^{1/2}$$

where A is the electrode surface area and C is the concentration of Fc-PDA in the vesicles on the sol-gel. It is convenient to calculate the $D_{app}$ from the slope of an Anson plot.

Vesicle solutions with concentrations from $0.38\times10^{-6}$ to $1.50\times10^{-6}$ M of Fc-PDA were prepared and adsorbed on the sol-gel surface of the electrodes. Linear Q vs. $t^{1/2}$ plots were obtained in the entire time window investigated (10 ms–5 s), indicating the diffusion control of the process. The slopes of these lines were from 0.64 to 1.76 $\mu C/s^{1/2}$, and the $D_{app}$ measurements were calculated to be in the range of $4.73\times10^{-8}$ to $2.30\times10^{-8}$ $cm/s^2$ for the surface coverage from $5.7\times10^{-12}$ $mol/cm^2$ to $2.25\times10^{-11}$ $mol/cm^2$. No dependence of $D_{app}$ on redox concentration was found, and the diffusion coefficients showed a descending trend with respect to redox concentration. Apparently, the rate-determining step of the overall charge-transport process is not the electron-exchange process (hopping) but another step. The lack of concentration dependence suggests that the electroreactivity is a mean-field behavior (i.e., charge propagation occurs via physical displacement of the redox element). Considering the unique surface morphology used in these experiments, it was believed that a lateral diffusion mechanism may be occurring on the liposome's bilayer membrane. The measured diffusion coefficients fall into the same magnitude as reported by Majda, and agree well with those measured by other groups using fluorescence recovery after photobleaching (FRAP) and NMR methods. Comparing this value to the diffusion coefficient obtained in redox polymers with fixed sites, the former was found to be about 2–3 orders of magnitude larger. The high $D_{app}$ in vesicles is likely a result of long-range lateral fluidity of the bilayer membranes, which has been suggested to stem from axial rotation of the lipid molecules around the bilayer normal. However, complete understanding of $D_{app}$ could be complicated. Indeed, such an understanding is not necessary in order to use the present invention. One could not totally rule out the contribution from electron hopping in this case, particularly in the boundary of liposomes adjacent to each other. It is belived that when lateral diffusion of lipids across the vesicle boundary appears to be unlikely, electron transport by percolation should prevail.

*E coli* LT toxin was chosen for this work because of its ready availability, and because it is representative of various other toxins. Examples of other toxins which can sub the *E. coli* LT toxin include those included in Table 2, below, which will produce equivalent results. In addition to these toxins, others include, but are not limited to *Pseudomonas aeruginosa* exotoxin A, *Streptococcus pneumoniae* pneumolysin, *B. cereus* cerelysin O, *Listeria monocytogenes* listeriolysin O, *Staphylococcus aureus* δ toxin, and *Aeromonas hydrophila* aerolysin. However, it is not intended that the present invention be limited to use with toxins. Indeed, it is contemplated that in addition to microbial toxins, the present invention will find use in the detection and/or identification of microorganisms, prions, antigens and/or antibodies, antigen and antibody complexes, and other suitable compounds or compositions of interest.

TABLE 2

Additional Detectable Toxins

| Toxin | Source | Activity |
|---|---|---|
| Anthrax toxin (EF) | *Bacillus anthracis* | Edema factor (EF) is an adenylate cyclase that causes increased levels in intracellular cAMP in phagocytes and formation of ion-permeable pores in membranes (e.g., hemolysis) |
| Anthrax toxin (LF) | *Bacillus anthracis* | Lethal factor (LF) is a $Zn^{++}$-dependent protease that induces cytokine release and is cytotoxic to cells by an unknown mechanism |
| Cereus toxin | *Bacillus cereus* | ADP-ribosylation of Rho; depolymerization of F-actin in cells |
| Adenylate cyclase toxin | *Bordetella pertussis* | Acts locally to increase cAMP levels in phagocytes and formation of ion-permeable pores in membranes (hemolysis) |
| Cholera enterotoxin | *Vibrio cholerae* | ADP ribosylation of G proteins stimulates adenylate cyclase and increases cAMP in cells of gastrointestinal tract, causing secretion of water and electrolytes |
| *E. coli* LT toxin | *E. coli* | Similar to cholera toxin |
| *E. coli* ST toxin | *E. coli* | Stimulates guanylate cyclase and promotes secretion of water and electrolytes from intestinal epithelium |
| Shiga toxin | *Shigella dysenteriae* | Enzymatically cleaves rRNA resulting in inhibition of protein synthesis in susceptible cells |
| Perfringens enterotoxin | *Clostridium perfringens* | Stimulates adenylate cyclase, leading to increased cAMP levels in epithelial cells |
| Alpha toxin | *C. perfringens* | Calcium-dependent phospholipase which hydrolyzes membrane phospholipids |
| Iota toxin | *C. perfringens* | Acts on SDP-ribosylation of actin to inhibit actin polymerization and depolymerization of F-actin |
| C2 toxin | *C. botulinum*, type C, D | Acts on SDP-ribosylation of actin to inhibit actin polymerization and depolymerization of F-actin |
| C3 toxin | *C. botulinum*, type C, D | ADP-ribosylation of rho; depolymerization of F-actin in cells |
| Botulinum toxin | *C. botulinum* | $Zn^{++}$-dependent protease that inhibits neurotransmission at neuromuscular synapses, resulting in flaccid paralysis |
| Tetanus toxin | *C. tetani* | $Zn^{++}$-dependent protease that inhibits neurotransmission at inhibitory synapses, resulting in spastic paralysis |
| Spiroforme toxin | *C. spiroforme* | Acts on SDP-ribosylation of actin to inhibit actin polymerization and depolymerization of F-actin |
| Enterotoxin A | *C. difficile* | Glucosylation of Rho, Rac, Cdc42; depolymerization of F-actin in cells |
| Cytotoxin B | *C. difficile* | Glucosylation of Rho, Rac, Cdc42; depolymerization of F-actin in cells |
| Lethal toxin | *C. sordelli* | Glucosylation of Rho, Rac, Cdc42; depolymerization of F-actin in cells |

TABLE 2-continued

Additional Detectable Toxins

| Toxin | Source | Activity |
|---|---|---|
| C3 toxin | *C. limosum* | ADP-ribosylation of rho; depolymerization of F-actin in cells |
| ActA | *Listeria monocytogenes* | Polymerization of actin in cells |
| Diphtheria toxin | *Corynebacterium diphtheriae* | ADP ribosylation of elongation factor 2 leads to inhibition of protein synthesis in target cells |
| Exotoxin A | *Pseudomonas aeruginosa* | Inhibits protein synthesis; similar to diphtheria toxin |
| Pertussis toxin | *Bordetella pertussis* | ADP ribosylation of G protein blocks inhibition of adenylate cyclase in susceptible cells |
| Staphylococcal enterotoxin | *Staphylococcus aureus* | Massive activation of the immune system, incuding lymphocytes and macrophages; leads to emesis |
| Toxin A | *S. aureus* | Membrane-acting toxin which affects transmembrane channel formation |
| Toxic shock syndrome toxin* (TSST-1) | *S. aureus* | Acts of vascular system, causing inflammation, fever and shock |
| Exfoliatin toxin* | *S. aureus* | Cleavage of epidermal cells (intradermal separation) |
| Erythrogenic toxin (scarlet fever toxin)* | *Streptococcus pyogenes* | Causes localized erythematous reactions |

From the above, it is clear that the present invention will find use in various settings, including for the identification of a wide variety of molecules other than toxins, including but not limited to pathogens, drugs, receptor ligands, antigens, ions, hormones, blood components, disease indicators, cell components, antibodies, lectins, enzymes, organic solvents, volatile organic compounds, pollutants, and genetic material).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in this or related fields are intended to be within the scope of the following claims.

We claim:

1. A method for measuring biomolecular recognition of at least one toxin by electrochemistry, comprising:
   a) providing:
      i) an electrode,
      ii) an insulator, and
      iii) liposomes having oxidation/reduction receptors, wherein said liposomes comprise a glycine-terminated diacetylene lipid, an acetylferrocenic diacetylene lipid comprising ferrocene, and a glycosphingolipid, and wherein said glycosphingolipid is known to be a receptor for at least one toxin;
   b) adding a sample suspected of containing at least one toxin to said liposomes; and
   c) measuring the current through said ferrocene to determine the biomolecular recognition of said at least one toxin by said liposomes, wherein a drop in said current is indicative of specific biomolecular recognition.

2. The method of claim 1, wherein said at least one toxin is an enterotoxin.

3. The method of claim 2, wherein said enterotoxin is *E. coli* enterotoxin.

4. The method of claim 3, wherein said receptor is a receptor for 84-kDa *E. coli* enterotoxin.

5. The method of claim 1, wherein said measuring is conducted by voltammetric determination.

6. The method of claim 1, wherein said insulator is a sol-gel thin film.

7. The method of claim 6, wherein said sol-gel thin film bears microcracks.

8. A method for measuring biomolecular recognition of a toxin by electrochemistry, comprising:
 a) providing:
  i) an electrode,
  ii) an insulator,
  iii) liposomes having oxidation/reduction receptors, wherein said liposomes comprise a glycine-terminated diacetylene lipid, an acetylferrocenic diacetylene lipid comprising ferrocene, and a glycosphingolipid, and wherein said glycosphingolipid is known to be a receptor for the 84-kDa *E. coli* enterotoxin, and
  iv) a sample suspected of containing *E. coli* enterotoxin;
 b) adding said sample to said liposomes; and
 c) measuring the current through said ferrocene to determine the biomolecular recognition of said *E. coli* enterotoxin by said liposomes, wherein a drop in said current is indicative of specific biomolecular recognition.

9. The method of claim 8, wherein the mixture ratio of glycine-terminated diacetylene lipid, acetylferrocenic diacetylene lipid, and a glycosphingolipid known to be a receptor of 84-kDa *E. coli* enterotoxin is approximately 4:1:0.25 respectively.

10. The method of claim 8, wherein said measuring is conducted by voltammetric determination.

11. The method of claim 8, wherein said insulator is a sol-gel thin film.

12. The method of claim 11, wherein said sol-gel thin film bears microcracks.

13. A method for measuring biomolecular recognition of an analyte by electrochemistry, comprising:
 a) providing:
  i) an electrode,
  ii) an insulator,
  iii) liposomes having oxidation/reduction receptors, wherein said liposomes comprise a glycine-terminated diacetylene lipid, an acetylferrocenic diacetylene lipid comprising ferrocene, and a glycosphingolipid, and wherein said glycosphingolipid is known to be a receptor of an analyte, and
  iv) a sample suspected of containing at least one analyte;
 b) adding said sample to said liposomes, and
 c) measuring the current through said ferrocene to determine the biomolecular recognition of the analyte by said liposomes, wherein a drop in said current is indicative of specific biomolecular recognition.

14. The method of claim 13, wherein the analyte is selected from the group consisting of microorganisms, drugs, receptor ligands, antigens, allergens, ions, hormones, blood components, disease indicators, cell components, antibodies, lectins, enzymes, organic solvents, volatile organic compounds, pollutants, and genetic material.

15. The method of claim 14, wherein said microorganism is a pathogen.

16. The method of claim 14, wherein said microorganism is selected from the group consisting of viruses, bacteria, parasites, fungi, and prions.

17. The method of claim 16, wherein said virus is selected from the group consisting of influenza, rubella, varicella-zoster, hepatitis A, hepatitis B, herpes simplex, polio, small pox, human immunodeficiency virus, vaccinia, rabies, Epstein Barr, reoviruses, and rhinoviruses.

18. The method of claim 13, wherein said insulator is a sol-gel thin film.

19. The method of claim 18, wherein said sol-gel thin film bears microcracks.

* * * * *